United States Patent [19]

Burgos

[11] Patent Number: 4,860,771
[45] Date of Patent: Aug. 29, 1989

[54] HOSPITAL SHEET

[76] Inventor: Stephen W. Burgos, 1441 Kapiolani Blvd. #1005, Honolulu, Hi. 96814

[21] Appl. No.: 210,793

[22] Filed: Jun. 24, 1988

[51] Int. Cl.[4] ............................................. A61F 13/00
[52] U.S. Cl. ...................................... 128/872; 128/876
[58] Field of Search ............ 128/869, 870, 871, 872, 128/873, 874, 875, 876, 849, 853, 854, 855; 604/349, 353, 388, 389, 350, 391, 394, 395, 399, 400; 5/494, 498, 504

[56] References Cited

U.S. PATENT DOCUMENTS

| | | | |
|---|---|---|---|
| 1,403,873 | 1/1922 | Scott | 128/872 |
| 1,556,747 | 10/1925 | Bates, Jr. | 128/872 |
| 2,201,662 | 5/1940 | Deluco | 604/388 |
| 2,456,898 | 11/1948 | Strandhagen | 128/870 |
| 2,486,114 | 10/1949 | Cataldo | 128/876 |
| 2,566,046 | 8/1951 | Weinstein | 128/870 |
| 2,586,961 | 2/1952 | Klein | 128/872 |
| 2,589,708 | 3/1952 | Koster | 128/873 |
| 2,698,620 | 1/1955 | Larkins | 604/394 |
| 2,700,778 | 2/1955 | Syracuse | 128/872 |
| 2,995,407 | 8/1961 | Izzi | 128/873 |
| 3,566,864 | 3/1971 | Garrow | 128/874 |
| 3,916,901 | 11/1975 | Korgemets | 604/392 |
| 4,050,737 | 9/1977 | Jordan | 297/465 |
| 4,117,840 | 10/1978 | Rasure | 128/874 |
| 4,672,958 | 6/1987 | Garman | 128/873 |
| 4,745,926 | 5/1988 | Hlusko | 128/873 |

FOREIGN PATENT DOCUMENTS 2042342 9/1980 United Kingdom ............... 604/349

*Primary Examiner*—Robert A. Hafer
*Assistant Examiner*—Michael Brown
*Attorney, Agent, or Firm*—Poms, Smith, Lande & Rose

[57] ABSTRACT

A reusable hospital sheet for a patient that can be tied to the hospital bed and wrapped around the patient. The sheet keeps the patient in place on the bed preventing sliding of the patient even if the bed is tilted or raised. An opening may be provided in the sheet for exiting of tubes from the lower abdomen of the patient, such as for catheters, rectal tubes, drainage tubes, etc.

13 Claims, 2 Drawing Sheets

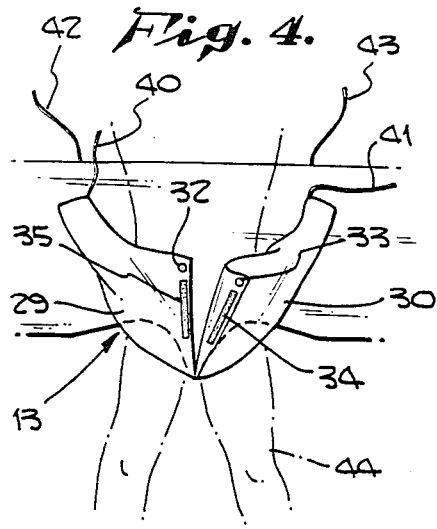
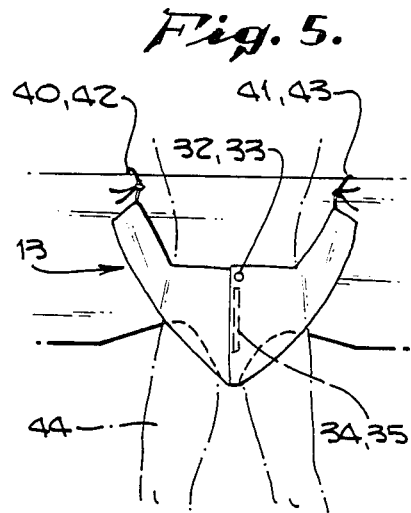
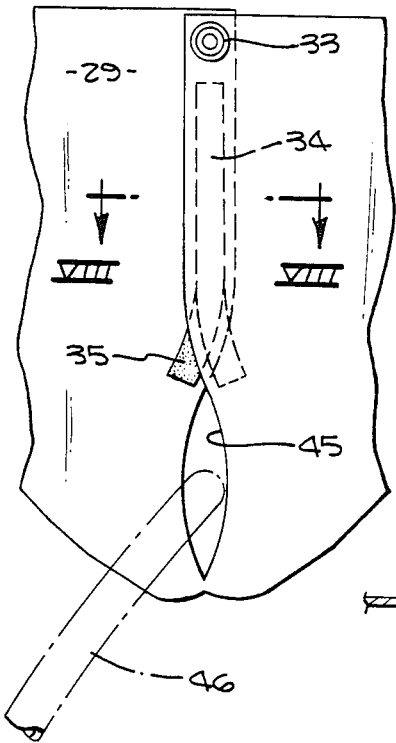
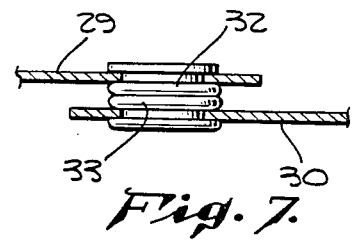
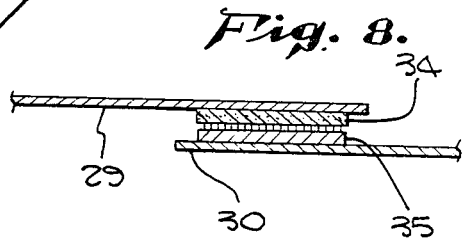

HOSPITAL SHEET

BACKGROUND OF THE INVENTION

1. Field of the Invention

The invention relates to hospital sheets; and, more particularly, to a reusable sheet attachable to a hospital bed for keeping the patient in a fixed position on the bed.

2. Description of the Prior Art

There is a need for holding a patient in a fixed position on a hospital bed. The patient should be held to the bed in a manner which prevents sliding of the patient up and down or side to side on the bed even if the bed is tilted, or falling out of bed. Also, it is necessary to easily and quickly reposition the patient on the bed to prevent decubiti. Such a device is necessary to both hold the patient yet permitting the exiting of tubes from the lower abdomen and to allow access to surgical incision sites.

Various prior art restraints are known but are deemed not practical. In U.S. Pat. No. 3,566,864, there is disclosed an infant safety garment but no access to the lower abdomen is provided. In U.S. Pat. No. 2,486,114 to Cataldo, a safety belt for infants is disclosed. There is no suggestion to use the same as a bed sheet.

There thus exists a need for a hospital sheet for patients, particularly debilitated, weak, elderly or disoriented patients, which retains the patient in a fixed position on the bed regardless of the orientation of the bed yet permits easy and quick repositioning of the patient to prevent decubiti and allows access to the lower abdomen. Such a sheet should be reusable and be able to withstand harsh treatment encountered in conventional hospital laundry facilities.

SUMMARY OF THE INVENTION

It is an object of this invention to provide a hospital sheet for retaining a patient in a fixed position on a hospital bed regardless of the orientation of the bed.

It is a further object of this invention to carry out the foregoing object in a manner allowing quick and easy re-positioning of the patient on the bed to prevent decubiti.

It is still further an object of this invention to carry out the foregoing objects in a manner permitting access to the lower abdomen of the patient for the exiting of tubes or the like or for access to surgical incision sites.

These and other objects are preferably accomplished by providing a reusable hospital sheet for a patient that can be tied to the hospital bed and wrapped around the patient. The sheet keeps the patient in place on the bed preventing sliding of the patient even if the bed is tilted or raised. An opening may be provided in the sheet for exiting of tubes from the lower abdomen of the patient, such as for catheters, rectal tubes, drainage tubes, etc.

BRIEF DESCRIPTION OF THE DRAWINGS

FIGS. 4 and 5 are illustrative views showing successive steps in securing the bed sheet of FIGS. 1 to 3 to a patient;

FIG. 6 is a detailed view of a portion of the bed sheet of FIGS. 1 to 3, in the position shown in FIG. 5, illustrating access to the lower abdomen of the patient;

FIG. 7 is a view taken along lines VII—VII of FIG. 6; and

FIG. 8 is a view taken along lines VIII—VIII of FIG. 6.

DESCRIPTION OF THE PREFERRED EMBODIMENT

Figure 1:
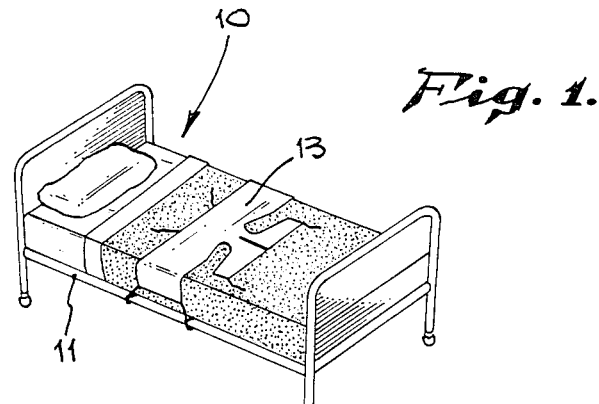
FIG. 1 is a perspective view of a conventional hospital bed with a bed sheet in accordance with the teachings of the invention tied thereto.
Figure 2:
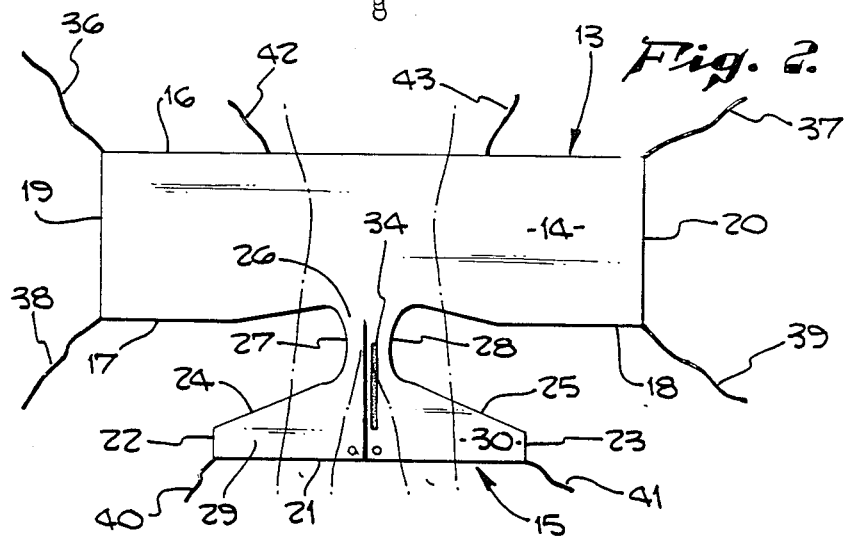
FIG. 2 is a top plan view of the bed sheet alone of FIG. 1.
Figure 3:
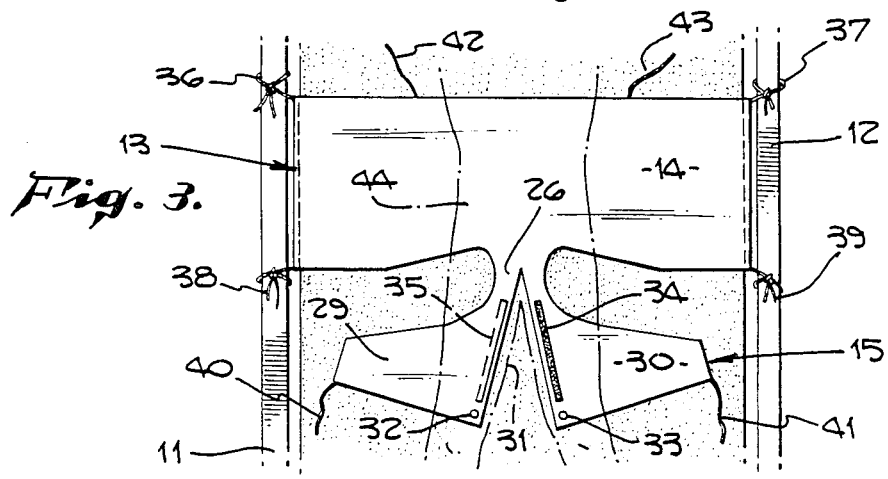
FIG. 3 is a top plan view of a portion of the bed of FIG. 1 showing a patient in outline thereon.

Referring to FIG. 1 of the drawing, a conventional hospital bed 10 is shown having side rails 11, 12 (see also FIG. 3). A bed sheet 13 is shown tied to bed 10 as will be discussed. Bed sheet 13 is shown in FIG. 2 having an upper generally elongated planar panel portion 14 and a lower trapezoidal portion 15. Portion 14 is defined by an upper elongated side 16, a pair of spaced lower elongated sides 17, 18 and interconnecting short sides 19, 20, respectively.

The lower trapezoidal portion 15 has an elongated lower side 21, short spaced sides 22, 23 at each respective end, and upwardly and inwardly angled sides 24, 25, respectively extending from sides 22, 23. The apex of portion 15 and the middle of portion 14 is joined by a neck portion 26. As seen in FIG. 2, side 21 may be shorter than side 16 and the neck portion 26 may be provided by cutting out like configured areas from a blank. That is, sides 17, 24 and arcuate area 27 may be formed by cutting out a portion from a blank or planar sheet conforming to sides 17, 24 and area 27. In like manner, sides 18, 25 and arcuate area 28 may be likewise so formed.

As seen in FIGS. 2 and 3, portion 15 may be divided down the middle into two separate sections, such as sections 29, 30 (FIG. 3), which are joined at neck portion 26 and can be moved together as in FIG. 2 or separated to form a V-shaped opening 31 as in FIG. 3. As seen in FIG. 3, mating snaps 32, 33 may be provided at the bottom inner end of each section 29, 30 for releasably securing these sections 29, 30 together. Also, mating strips of a releasable interconnecting material, such as Velcro strips 34, 35 may be provided along the inner side edges of each respective section 30, 29, as shown (strip 35 indicated in dotted lines).

A plurality of elongated flexible elements, such as cords, are provided for releasably securing sheet 13 to side rails 11, 12 and to other parts of sheet 13, as will be discussed (or end rails or other areas of the bed 10, if desired). Thus, flexible members 36, 37 are provided at each respective end of side 16 and flexible members 38, 39 are provided at each outer end of sides 17, 18, respectively. Flexible members 40, 41 are provided at each end of lower side 21 and a pair of flexible members 42, 43 are provided at spaced locations along side 16 of upper portion 14.

As seen in FIGS. 1 and 3, sheet 13 is laid across the bed 10 and members 36, 38 are tied to side rail 11 whereas members 37, 39 are tied to side rails 12. The patient 44 (FIG. 3) then is placed on top of sheet 13. The lower parts or halves 29, 30 are folded up over the lower torso of the patient as seen in FIG. 4, and cords 40, 42 and cords 41, 43 are tied together (FIG. 5). Velcro strips 34, 35 (FIG. 4) are brought together (FIGS. 5 and 8) and snaps 32, 33 are snapped together (FIGS. 5 and 7). If desired as seen in FIG. 6, the Velcro strips 34, 35 can be parted slightly at the bottom to provide an opening 45 through which tubing 46 can extend. This opening 45 can be made as large as desired.

Sheet 13 can be quickly and easily cut out of a flat planar sheet of material, such as cloth, and is preferably washable so as to be reusable. Any suitable material may be used but a material that will hold up under normal hospital abuse and repeated washings is preferred.

It can be seen that there is disclosed a hospital sheet in the preferred form of a flat planar rectangular piece of fabric material that wraps around the patient. Four cords or strings at the four corners tie the sheet to the side rails of a hospital bed. In this way, the patient is kept in place, not allowing him or her to fall out of bed, nor slide up or down or right or left, which is a problem if the bed is tilted or if the patient is partially sitting. This prevents the necessity of multiple repositioning of the patient. Since the sheet can be tied firmly or loosely to the side rails, it is possible to place rolled towels and pillows under the patient's right or left hip to allow him or her to be positioned as desired on the bed to prevent decubiti. Thus, the sheet will be most useful with debilitated, weak, elderly, or disoriented patients. The sheet also allows for the exiting of tubes from the lower abdomen (e.g., Foley catheters, rectal tubes, surgical drainage tubes) as well as allowing access to surgical incision sites on the patient. The sheet is preferably re-usable and should withstand punishment in hospital laundry facilities.

Sheet 13 can be of any suitable dimensions. Although bottom portion 15 has been shown as having a bottom edge 21 shorter than edge 16 of upper portion 14, obviously, edge 21 can be longer, if desired. The overall width of upper and lower portions 14, 15, and of course the overall length of sheet 13, is chosen to enable the sheet 13 to wrap around the body of a patient and be tied thereto. The flexible material of sheets 13 and the flexible cords allows for quite a bit of variation to accommodate to patients of differing sizes. Of course, sheets 13 in varying sizes may also be provided.

I claim:

1. A hospital bed sheet adapted to be tied to a hospital bed and wrapped around a patient to hold the latter in a fixed position with respect to the bed comprising:
    an elongated rectangular planar upper portion having a longitudinal axis;
    a lower portion joined to the upper portion by a neck portion, said lower portion being comprised of a pair of separable sections releasably connected to each other along a line formed when said separable sections are joined together extending generally normal to said longitudinal axis of said upper portion;
    first flexible connecting means at each corner of said upper portion for securing the same to the side rails of a hospital bed;
    said rectangular portion having an elongated upper edge with second flexible connecting means disposed at spaced locations along said upper edge inwardly of the ends of said edge; and
    said lower portion having an elongated lower edge with third flexible means disposed at each end of said lower edge whereby said first flexible means can be connected to the side rails of a hospital bed and said lower portion can be folded up over the lower torso of a patient about said neck portion with said second and third flexible means connected to each other to thereby secure said patient in a fixed position with respect to said bed.

2. In the sheet of claim 1 wherein said upper, lower and neck portions are formed from a single planar sheet.

3. In the sheet of claim 1 wherein said upper, lower and neck portions are of cloth material.

4. In the sheet of claim 1 wherein, said lower portion is trapezoidally-shaped, said trapezoidally-shaped lower portion having an upper apex said lower edge comprising the bottom edge of said trapezoid, said upper apex of said trapezoid being joined to said neck portion.

5. In the sheet of claim 1 wherein said separable sections further comprise mating edges that are releasably connected together by elongated strips of mating Velcro material.

6. In the sheet of claim 5 wherein said strips extend along the mating side edges of each separable sections generally parallel to said line extending generally normal to the longitudinal axis of said upper portion when said separable sections are joined together.

7. In the sheet of claim 1 wherein said separable sections are further releasably connected together by mating snaps.

8. A planar sheet for a hospital bed comprising a single planar sheet of flexible material having an elongated upper edge, a first side edge extending downwardly from one end of said upper edge in a direction normal thereto, a second side edge extending downwardly from a second end of said upper edge in a direction normal thereto, a, first middle edge extending from said first side edge and inwardly of said sheet spaced from and generally parallel to said upper edge, a second middle edge extending from said second side edge inwardly of said sheet spaced from and generally parallel to said upper edge and terminating before said first middle edge, an elongated bottom edge spaced from and generally parallel to said upper edge, a third side edge extending upwardly from one end of said bottom edge in a direction normal thereto, a fourth side edge extending upwardly from a second end of said bottom edge in a direction normal thereto, a first tapered edge extending from said third side edge inwardly and upwardly and curving into engagement with said first middle edge, a second tapered edge extending from said fourth side edge inwardly and upwardly and curving into engagement with said second middle edge, said bottom edge and said third and fourth side edges and said first and second tapered edges forming a lower portion of said sheet separated into two separate parts along a line extending upwardly from generally said midpoint, of said bottom edge a short distance toward an upper portion of said sheet which is comprised of said upper edge, said first and second side edges and said first and second middle edges.

9. In the sheet of claim 8 wherein said sheet is of cloth material.

10. In the sheet of claim 8 wherein said bottom edge is shorter in overall length than said upper edge.

11. In the sheet of claim 8 including flexible cords at each outer corner of said upper portion, at each end of said bottom edge and at spaced locations along said upper edge.

12. In the sheet of claim 8 including releasable securing means on each separate part of said lower portion adjacent the line of separation.

13. In the sheet of claim 12 wherein said releasable securing means comprises mating strips of Velcro material.

* * * * *